(12) United States Patent
Haubennestel et al.

(10) Patent No.: US 7,652,166 B2
(45) Date of Patent: Jan. 26, 2010

(54) BIURET COMPOUNDS, THEIR PREPARATION AND USE, AND INTERMEDIATES IN THEIR PREPARATION

(75) Inventors: Karlheinz Haubennestel, Wesel (DE); Stefan Moessmer, Wesel (DE); Ulrich Orth, Wesel (DE); Daniela Betcke, Wesel (DE)

(73) Assignee: BYK-Chemie GmbH (DE)

( * ) Notice: Subject to any disclaimer, the term of this patent is extended or adjusted under 35 U.S.C. 154(b) by 665 days.

(21) Appl. No.: 11/400,721

(22) Filed: Apr. 7, 2006

(65) Prior Publication Data

US 2006/0276675 A1 Dec. 7, 2006

(30) Foreign Application Priority Data

Apr. 7, 2005 (DE) .................. 10 2005 015 966

(51) Int. Cl.
| | |
|---|---|
| C07C 271/58 | (2006.01) |
| C07C 271/52 | (2006.01) |
| C07C 271/34 | (2006.01) |
| C07C 271/36 | (2006.01) |
| C07C 271/38 | (2006.01) |
| C07C 271/24 | (2006.01) |
| C07C 271/28 | (2006.01) |
| C07C 271/20 | (2006.01) |
| C07C 275/40 | (2006.01) |
| C07C 275/18 | (2006.01) |
| C07C 275/14 | (2006.01) |
| C07C 269/06 | (2006.01) |

(52) U.S. Cl. ................... 560/25; 560/26; 560/115; 560/158; 564/38

(58) Field of Classification Search .......... 560/25, 560/26, 115, 158; 564/38
See application file for complete search history.

(56) References Cited

U.S. PATENT DOCUMENTS

| 4,882,408 | A | 11/1989 | Blum |
| 6,420,466 | B1 | 7/2002 | Haubennestel et al. |
| 2005/0250927 | A1 | 11/2005 | Pritschins et al. |

FOREIGN PATENT DOCUMENTS

| DE | 3502683 A1 | 8/1986 |
| DE | 3724555 A1 | 2/1989 |
| DE | 19919482 C2 | 4/2001 |
| EP | 1048681 A2 | 11/2000 |
| EP | 1593700 A1 | 11/2005 |

OTHER PUBLICATIONS

"European Patent Application No. 06007037.2, European Search Report mailed Nov. 12, 2007", 6 pgs.
Kricheldorf, H. R., et al., "$^{15}$N NMR Spectroscopy 27. Spectroscopic Characterization of Polyurethanes and Related Compounds", *Makromolekulare Chemie*, 182(2) (1981), 1177-1196.
Reemers, S., et al., "Novel Route to Dendritic Structures and Their Application for Surface Modification", *Journal of Polymer Science, Part A: Polymer Chemistry*, 44(4), (2005), 1372-1386.
Singh, P., et al., "Studies on the Stability of the Dimer of 2, 4-Tolylene DiIsocyanate", *Canadian Journal of Chemistry*, 40, (1962), 935-940.

*Primary Examiner*—Peter G O'Sullivan
(74) *Attorney, Agent, or Firm*—Schwegman, Lundberg & Woessner, P.A.

(57) ABSTRACT

The present invention relates to biuret compounds of the general formula

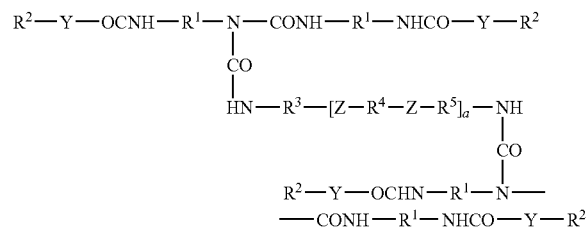

in which $R^1$ is $C_2$-$C_{18}$ alkylene, cycloalkylene, arylene or aralkylene, Y is —O— and/or —NH—, $R^2$ is $C_4$-$C_{22}$ alkyl, $C_3$-$C_{18}$ alkenyl, cycloalkyl, aralkyl, $C_mH_{2m+1}(O$—$C_nH_{2n})_x$—(O—CH($C_6H_5$)—$CH_2)_{u}$-, $C_mH_{2m+1}(OOC$—$C_vH_{2v})_x$-, X—$C_6H_4$—(O—$C_nH_{2n})_x$—(O—CH($C_6H_5$)—$CH_2)_{u}$-, where m=1-22, n=2-4, x=0-15, u=0-15, v=4-5, X is $C_1$-$C_{12}$ alkyl, —($C_6H_5)_{1-4}$ and $R^3$, $R^4$ and $R^5$ are $C_2$-$C_{18}$ alkylene, cycloalkylene, arylene or aralkylene, it being possible for $R^3$, $R^4$ and $R^5$ to be identical or different, Z is —COO—, NHCO—, NHCOO—, NHCONH— and/or mixtures thereof and a is 1-20. The invention also relates to a process for preparing biuret compounds and to their use as rheology control agents. The invention further relates to urethane- and/or urea-containing uretdiones which are useful intermediates for preparing the biuret compounds.

7 Claims, No Drawings

BIURET COMPOUNDS, THEIR PREPARATION AND USE, AND INTERMEDIATES IN THEIR PREPARATION

RELATED APPLICATION

This application claims priority under 35 U.S.C. 119 to German Application No. 10 2005 015 966.4, filed Apr. 7, 2005, which application is incorporated herein by reference and made a part hereof.

The present invention relates to biuret compounds, processes for preparing them and their use. It also relates to urethane- and/or urea-containing uretdiones which are useful intermediates for preparing the biuret compounds of the invention.

The biuret compounds of the invention are suitable for use as thixotropic agents for coating systems such as for example, solvent-borne, solvent-free and aqueous paints, PVC plastisols, epoxy-based coatings and coatings based on unsaturated polyester resins.

In order to control the rheology of liquid coating systems it is common to use silicas, hydrogenated castor oil or organically modified bentonites, as described, for example, in U.S. Pat. Nos. 4,208,218, 4,410,364 and 4,412,018. Furthermore, polyamide waxes are widely employed. Specifically in the field of polyamides and polyamide esters, there exist numerous patents, such as DE 69523221, EP 0528363, EP 0239419, U.S. Pat. Nos. 5,510,452 and 5,349,011.

Use is also made, however, of combinations of modified bentonites with polyamides, as described in EP 0509202 and DE 69704691.

A disadvantage of these substances is that they are generally dry solids or pastes which have to be transferred into a semi-finished product using solvents and shear forces and introduced into the liquid coating system by means of targeted temperature control. If these temperatures are not maintained, crystallites occur in the finished coating system and lead to defects in the coating. The general disadvantage of these systems is that they lead to turbidity and haze in clear, transparent coatings. Moreover, handling dry products which give rise to dust during processing is undesirable.

The polyamide esters are frequently liquid and are therefore much less effective than the inherently solid substances.

Other solutions for rheology control have been presented in patent application EP 0 198 519. There, an isocyanate is reacted with an amine in the presence of binders to form a urea which in very finely dispersed form forms acicular crystals. These binders thus modified are offered as rheology-controlling and sag-preventing binders, referred to as "sag control agents".

The disadvantage of these products is that they are always tied to the binders in which they have been prepared and do not allow subsequent universal correction of ready-produced coating material.

Patent application EP 0 006 252 describes a process for preparing a thixotropic agent that removes some of the above disadvantages, describing urea urethanes which are prepared in aprotic solvents in the presence of LiCl by reaction of isocyanate adducts with polyamines. The disadvantage of the products thus prepared lies in the undefined structure of these urea urethanes, which is a consequence of the preparation process. In this process 1 mol of a diisocyanate is first reacted with 1 mol of a monoalcohol. This produces the desired NCO functional monoadducts, but also non-NCO functional diadducts. Furthermore a certain fraction of monomeric diisocyanate remains unreacted. The fractions of these various compounds are variable, depending on the availability of the NCO group and the reaction conditions, such as temperature and time. All of these adducts prepared in this way, however, contain relatively large amounts of unreacted diisocyanate, which on further reaction with polyamines leads to uncontrolled chain extension of the molecule. These products tend to precipitation or undesired gelling and, accordingly, to seeding in the binder. In patent application DE 19919482 these disadvantages are circumvented by removal of the excess isocyanate. These products, however, have the disadvantage that they yield stable solutions only in high-polarity solvents such as N-methylpyrrolidone for example, with the assistance of alkali metal salts.

It is the object of the present invention to find a process which produces thixotropic agents of defined structure and thereby ensures an improved effect profile and improved reproducibility of thixotroping.

Surprisingly it has been found that this object can be achieved by means of biuret compounds which are preparable from uretdiones (component A) and diamines (component B) and have the general structure A-B-A.

The invention accordingly provides biuret compounds of the general formula

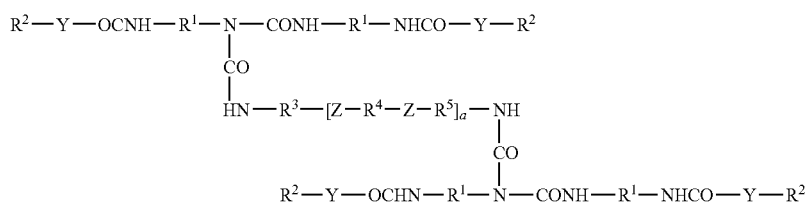

in which $R^1$ is $C_2$-$C_{18}$ alkylene, cycloalkylene, arylene or aralkylene, Y is —O— and/or —NH—, $R^2$ is $C_4$-$C_{22}$ alkyl, $C_3$-$C_{18}$ alkenyl, cycloalkyl, aralkyl, $C_mH_{2m+1}(O-C_nH_{2n})_x-(O-CH(C_6H_5)-CH_2)_u$-, $C_mH_{2m+1}(OOC-C_vH_{2v})_x$-, $X-C_6H_4-(O-C_nH_{2n})_x-(O-CH(C_6H_5)-CH_2)_u$-, where m=1-22, n=2-4, x=0-15, u=0-15, v=4-5, X is $C_1$-$C_{12}$ alkyl, —$(C_6H_5)_{1-4}$ and $R^3$, $R^4$ and $R^5$ are $C_2$-$C_{18}$ alkylene, cycloalkylene, arylene or aralkylene, it being possible for $R^3$, $R^4$ and $R^5$ to be identical or different, Z is —COO—, NHCO—, NHCOO—, NHCONH— and/or mixtures thereof and a is 1-20. In this context and throughout this application, the phrase "it being possible that certain substituents are identical or different means that the substituents may be independently chosen from the designated groups. For the foregoing substituents $R^3$, $R^4$ and $R^5$ this phrase means that selections from among the designated groups are independently chosen for each of the substituents.

Advantageously the radical $R^2$ is a polyalkoxymonoalcohol radical containing ethylene oxide and/or propylene oxide and/or butylene oxide groups.

The invention also provides a process for preparing biuret compounds in which uretdiones of the general formula (A)

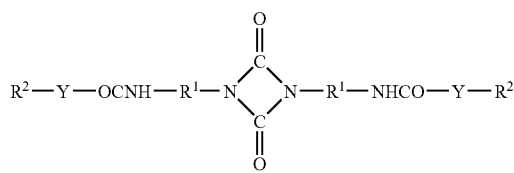

(A)

in which:

$R^1$ is $C_2$-$C_{18}$ alkylene, cycloalkylene, arylene or aralkylene,

Y is —O— and/or —NH—, $R^2$ is $C_4$-$C_{22}$ alkyl, $C_3$-$C_{18}$ alkenyl, cycloalkyl, aralkyl, $C_mH_{2m+1}(O-C_nH_{2n})_x-(O-CH(C_6H_5)-CH_2)_u$-, $C_mH_{2m+1}(OOC-C_vH_{2v})_x$-, $X-C_6H_4-(O-C_nH_{2n})_x-(O-CH(C_6H_5)-CH_2)_u$-, where m=1-22, n=2-4, x=0-15, u=0-15, v=4-5, and X is $C_1$-$C_{12}$ alkyl, or —$(C_6H_5)_{1-4}$, are reacted with diamines of the general formula (B)

(B)

in which:

$R^3$, $R^4$ and $R^5$ are $C_2$-$C_{18}$ alkylene, cycloalkylene, arylene or aralkylene, it being possible for $R^3$, $R^4$ and $R^5$ to be identical or different, (i.e., $R^3$, $R^4$ and $R^5$ are independently chosen from the designated groups).

Z is —COO—, NHCO—, NHCOO—, NHCONH— and/or mixtures thereof and a is 1-20.

In the preparation of the biuret compounds of the invention uretdione-containing polyisocyanates are first reacted, with retention of the uretdione moiety, with monoalcohols and/or monoamines to form urethane- and/or urea-containing polymers and in a second step the biuret compounds of the invention are prepared by reaction with polyamines, accompanied by opening of the uretdione ring.

Uretdiones, as the skilled person is aware, are prepared by addition reaction of monomeric diisocyanates using specific catalysts (H. J. Laas; R. Halpaap; J. Pedain; *J. prakt. Chemie* 336 (1994), 185-200). Preference is given to using HDI uretdione, which is available commercially as Desmodur N 3400 from Bayer and which in addition to the uretdione moiety contains HDI trimers and allophanates.

The monoalcohols used in the first step are aliphatic, cycloaliphatic and araliphatic alcohols. With regard to the aliphatic alcohols, linear, branched or cyclic alcohols with a chain length of C2-C22 are used, such as ethanol, propanol, n-butanol, octanol, decanol, dodecanol, oleyl alcohol and stearyl alcohol. Cycloaliphatic alcohols include, for example, cyclopentanol and cyclohexanol. Araliphatic alcohols such as benzyl alcohol, for example, likewise find use. Polymeric alcohols such as polyolefin monools, polyacrylate monools, polycarbonate monools, polycaprolactone monools or polysiloxane monools may likewise be used for the invention, as may fatty alcohol alkoxylates with a variable degree of alkoxylation, of the kind known to the skilled person under the trade name Lutensol from BASF. Polyalkoxy monoalcohols which contain ethylene oxide and/or propylene oxide and/or butylene oxide groups and which may have been modified with styrene oxide are preferred. Polyalkoxy monoalcohols such as, for example MPEG 350, MPEG 500 and MPEG 750, which are polyethylene glycols prepared starting from methanol and containing a terminal OH group are particularly preferred. The monoalcohols may also be used in mixtures.

The monoamines are aliphatic, cycloaliphatic and araliphatic amines. With regard to the aliphatic amines, linear, branched or cyclic amines having a chain length of C2-C22 are used, such as ethylamine, propylamine, isopropylamine, butylamine, sec- and tert-butylamine, 3-methyl-1-butanamine, hexylamine, 2-ethylhexylamine, octylamine, cyclopentylamine, cyclohexylamine, tridecylamine, oleylamine, octadecylamine and the mixtures of C 12-C 22 amines that are known under the trade name Armeen from Akzo Nobel. Amines in accordance with the invention are not only polyolefin amines such as polyisobutylenamine, for example, but also, preferably, polyoxyalkylenemonoamines, which contain ethylene oxide and/or propylene oxide groups and which are known under the trade name Jeffamine M 600, M 1000, M 2005 and M 2070 from Huntsman. The araliphatic amines are products such as for example, benzylamine and furfurylamine. It is also possible, however, to use hydrazides such as benzoic hydrazide, for example. The monoamines can also be used as mixtures, and it is also possible for the monoamines to be employed as a mixture in any proportion with the monoalcohols.

The reaction between the uretdione-containing polyisocyanate in the monoalcohol, with retention of the uretdione ring, is carried out at temperatures between 15 and 60° C., preferably between 20 and 50° C., where appropriate with the assistance of the catalyst, such as dibutyltin dilaurate (DBTL). The reaction between the uretdione-containing polyisocyanate and the monoamine, with retention of the uretdione ring, is carried out at temperatures between 15 and 45° C., preferably between 20 and 30° C. The sequence of addition of the co-reactants is generally arbitrary. The uretdione-containing polyisocyanate can be introduced initially where appropriate in an inert solvent, and the monoalcohol or monoamine is added dropwise. It is also possible for the monoalcohol or the monoamine to be introduced initially and the uretdione-containing polyisocyanate is added dropwise. If, on the other hand, a mixture of monoalcohol and monoamine is used, the uretdione-containing polyisocyanate is reacted first with the alcohol and subsequently with the amine. Where appropriate, the reaction can also be carried out in an inert solvent, such as methoxypropyl acetate, cyclohexane, toluene, xyolene or a higher-boiling aromatic such as Shellsol A, for example. N-Methylpyrrolidone or N-ethylpyrrolidone are likewise suitable as solvents.

The diamines of the general formula (B) are prepared by reacting polycarboxylic acids, preferably dicarboxylic acids and/or dicarboxylic anhydrides with diamines, the diamine:polycarboxylic acid ratio being between 2:1 and 20:9, preferably between 3:2 and 12:11 and more preferably between 4:3 and 8:7.

The diamines are preferably aliphatic and araliphatic primary diamines, such as ethylenediamine, neopentanediamine, 1,2- and 1,3-propanediamine, 1,6-hexamethylenediamine, 1,8-octamethylenediamine, 1,12-dodecamethylenediamine, cyclohexyldiamine, 4,4'-diaminodicyclohexylmethane, 3,3'-dimethyl-4,4'-diaminodicyclohexylmethane, isophoronediamine, 4,7-dioxadecane-1,10-diamine, 4,7,10-trioxadecane-1,13-diamine, polyoxyalkylenediamines containing ethylene oxide and/or propylene oxide groups in a random or blockwise arrangement, known under the trade names Jeffamine D and Jeffamine ED from Huntsman, having a number average molecular weight of between 148 and 4000 g/mol, and para- and meta-xylylenediamine. 1,6-hexamethylenediamine is preferred. It is also possible, however, to use hydrazides such as oxalic dihydrazide, succinic dihydrazide or adipic dihydrazide, for example. Mixtures of these diamines are also possible.

The polycarboxylic acids are preferably aliphatic, cycloaliphatic or aromatic, linear or branched, saturated or unsaturated dicarboxylic acids having at least 2, preferably between 3 and 40, carbon atoms. Examples of such polycarboxylic acids are adipic acid, oxalic acid, malonic acid, succinic acid, glutaric acid, pimelic acid, suberic acid, sebacic acid, azelaic acid, undecanedioic acid, 1,11-undecanedicarboxylic acid, didecanedioic acid, hexadecanedioic acid, docosanedioic acid, maleic acid, fumaric acid, terephthalic acid or isophthalic acid, used alone or in mixtures. Acid anhydrides such as maleic anhydride, glutaric anhydride, phthalic anhydride and succinic anhydride, which may have been modified with alkyl or alkylene groups, such as dodecenylsuccinic anhydride, for example, are also suitable. Polymeric polycarboxyic acids such as the dicarboxylic acid of polybutadiene, for example, may also be used, as may hydroxy-functional polycarboxylic acids such as tartaric acid, citric acid and hydroxyphthalic acid, for example. Oxydicarboxylic acids such as 3,6,9-trioxyundecanedioic acid and dicarboxypolyglycol are also included. Dimerized fatty acids, known to the skilled person as dimer acids, having a carbon length of 36 carbon atoms are preferred. These dimer acids may have either a low monomer content (usually <8 percent by weight), or a fraction of not more than 20 percent by weight of trimer acid.

The polycarboxylic acids may be replaced in whole or in part by diisocyanates and the diamines in whole or in part by diols, in which case ester, urethane and/or urea groups may be present alongside the preferred amide moieties in the polymer.

The diols are preferably polyalkylene polyols, polyalkenyl polyols, modified where appropriate with C1-C4 alkyl and/or alkoxy groups, or are polyether polyols, polyester polyols, mixed polyester polyether polyols, polycarbonate polyols, polyolefin polyols, polyacrylate polyols, polycaprolactone polyols and polysiloxane polyols having preferably 2 hydroxyl end groups.

Diisocyanates used may be aliphatic, cycloaliphatic and aromatic diisocyanates, alone or in mixtures. Examples of such diisocyanates are 1,4-tetramethylenediisocyanate, 1,6-hexamethylenediisocyanate, 2,2,4-trimethyl-1,6-hexamethylenediisocyanate, 1,10-decamethylenediisocyanate, 1,4-cyclohexylenediisocyanate, p-phenylenediisocyanate, m-phenylenediisocyanate, 2,6-toluenediisocyanate, 2,4-toluenediisocyanate and mixtures thereof, p- and m-xylylenediisocyanate, 4,4'-diisocyanatodicyclohexylmethane, 3,3'-dimethyl-4,4'-bisphenylenediisocyanate, 3,3'-dimethyldiisocyanatodiphenylmethane, the isomer mixtures of 2,4'- and 4,4'-diisocyanatodiphenylmethane, and $C_{36}$ dimer diisocyanate.

Diamines of the general formula (B) are prepared under conditions of the kind known to the skilled person. The reaction temperature during the condensation reaction of the dicarboxylic acids with diamines/diols is preferably between 100 and 250° C., more preferably between 140 and 200° C. The ratio of diamine to polycarboxylic acid is preferably chosen such that for n equivalents of polycarboxylic acid (n+1) equivalents of diamine are used, so that after the end of the reaction the condensation product has an amine number. The diamine:polycarboxylic acid ratio is between 2:1 and 20:19, preferably between 3:2 and 12:11, more preferably between 4:3 and 8:7. In the addition reaction of diisocyanates with diamines/diols the reaction temperature is preferably between 40 and 120° C., more preferably between 60 and 100° C.

To prepare the biuret compounds of the invention, the uretdiones in the general formula (A) and the diamines in the general formula (B) are reacted at a reaction temperature between 60 and 120° C., more preferably between 75 and 90° C. The ratio of components A and B in this case is chosen such that for 1 mol of A between 0.3 mol and 0.7 mol, preferably between 0.4 mol and 0.6 mol, more preferably between 0.5 mol, of B is used. The reaction can be carried out with or without solvent. Suitable solvents are all aliphatic, aromatic, protic and aprotic solvents such as, for example, methoxypropyl acetate, cyclohexane, toluene, xylene or higher-boiling aromatics such as Shellsol A, for example. N-Methylpyrrolidone or N-ethylpyrrolidone, and also alcohols such as ethanol, propanol, isobutanol or butylglycol, are likewise suitable. Mixtures of solvents can also be used.

The invention further provides for the use of the above-described addition compounds as rheology control agents, in particular as anti-sag agents and anti-settling agents, particularly in association with the use of heavy pigments which have a propensity towards severe settling, such as aluminium pigments and mica pigments. Thus, the invention includes a method for use of the inventive compounds to provide rheology control, anti-sag control and anti-settling control for coating systems such as for example, solvent-borne, solvent-free and aqueous paints, PVC plastisols, epoxy-based coatings and coatings based on unsaturated polyester resins and will as other similar polymeric coating compositions that may be cured or cross-linked to form an impervious surface.

However, in the case of polymeric coatings for industrial flooring, based on epoxy or polyurethane, or in the case of what are called gel coats, based on unsaturated polyester resins, rheology control agents are also of advantage and the addition compounds of the invention can be used here with advantage.

The present invention also provides the urethane- and/or urea-containing uretdiones of the general formula (A) and also processes for preparing them, in which uretdione-containing polyisocyanates are reacted, with retention of the uretdione moieties, with aliphatic, cycloaliphatic and/or araliphatic monoalcohols and/or mixtures thereof and/or aliphatic, cycloaliphatic and/or araliphatic monoamides and/or mixtures thereof. These uretdiones are new and useful intermediates for the preparation of the biuret compounds of the invention. The preparation of these intermediates has already been described in detail above.

The invention is elucidated further below with reference to examples.

Preparation of Inventive Component A:

EXAMPLE 1

A 1-litre 3-necked flask with stirrer, reflux condenser and thermometer is charged at room temperature in succession with 79.6 g (0.2 mol) of hexamethylene diisocyanate uretdione (Desmodur N3400 from Bayer) and 300 g (0.4 mol) of methoxypolyethylene glycol 750 and this initial charge is heated to 80° C. The reaction is taken to the point where isocyanate is no longer detectable. The reaction mixture is then cooled to 50° C.

Preparation of Inventive Component B:

EXAMPLE 2

A 1-litre 3-necked flask with stirrer, water separator and thermometer is charged in succession with 168 g (0.3 mol) of dimer acid, 46.4 g (0.4 mol) of hexamethylenediamine and 92 g of Shellsol A (highly aromatic hydrocarbon solvent, Shell) and this initial charge is heated slowly at 160° C. The water released slowly during the reaction is separated off azeotropically via the water separator. The reaction is at an end when the acid number is <3. The reaction mixture is subsequently cooled to 50° C.

Preparation of Inventive Biuret Adducts:

EXAMPLE 3

A 1-litre 3-necked flask with stirrer, reflux condenser and thermometer is charged in succession with 103.6 g (0.1 mol) of the reaction product from Example 1 and 153.1 g (0.05 mol) of the reaction product from Example 2 and the mixture is heated to 80° C. The reaction mixture is stirred for a further 3 hours until the amine number is <3. The product is then diluted with isobutanol to 50% solids.

Components A:

| Example | Uretdione | Amine/alcohol components |
|---|---|---|
| 4 | Hexamethylene diisocyanate uretdione | Oleyl alcohol |
| 5 | Hexamethylene diisocyanate uretdione | Oleylamine |
| 6 | Hexamethylene diisocyanate uretdione | Jeffamine M600 |
| 7 | Hexamethylene diisocyanate uretdione | Methoxypolyethylene glycol M350 |
| 8 | Hexamethylene diisocyanate uretdione | Methoxypolyethylene glycol M500 |
| 9 | Hexamethylene diisocyanate uretdione | Jeffamine M2070 |
| 10 | | |

Components B:

| Example | Dicarboxylic acid | Diamine | Dicarboxylic acid:diamine molar ratio |
|---|---|---|---|
| 11 | Dimer acid | Jeffamine ED 600 | 4:5 |
| 12 | Adipic acid | Jeffamine ED 900 | 5:6 |
| 13 | Dimer acid | Jeffamine ED 2003 | 5:6 |
| 14 | Adipic acid | m-Xylylenediamine | 3:4 |
| 15 | Adipic acid | Jeffamine ED 900 | 4:5 |
| 16 | Adipic acid | Jeffamine ED 2003 | 3:4 |
| 17 | Adipic acid/dimer acid ratio 2.1 | Jeffamine ED 600 | 4:5 |
| 18 | Adipic acid/dimer acid ratio 2.1 | Jeffamine ED 2003 | 4:5 |
| 19 | Adipic acid/dimer acid ratio 2.1 | m-Xylylenediamine | 4:5 |
| 20 | Adipic acid | Hexamethylenediamine | 4:5 |
| 21 | Dimer acid | Hexamethylenediamine | 4:5 |
| 22 | Dimer acid | m-Xylylenediamine | 4:5 |
| 23 | Dimer acid | m-Xylylenediamine/hexamethylenediamine 3:2 | 4:5 |

Biuret Adducts:

| Example | Component A | Component B |
|---|---|---|
| I | from Example 1 | from Example 2 |
| II | from Example 6 | from Example 11 |
| III | from Example 9 | from Example 13 |
| IV | from Example 1 | from Example 19 |
| V | from Example 5 | from Example 12 |

Performance Results:

The inventive products were tested in 2-component epoxy systems for their ability to form gels. Additionally, the achievable film thicknesses in the binders were ascertained. The two-component (2K) binder system employed was as follows:

1. Epikote 1001/Epikote 834, polyepoxides based on bisphenol A, Ancamide 700-X-75, high molecular mass diamine
2. Epikote 828, polyepoxides based on bisphenol A, Ancamide 700-X-75, high molecular mass diamine.

Test Formulation:

| | |
|---|---|
| Epikote 1001 (75%) in xylene | 34.5 g |
| Epikote 834 (80%) in xylene | 7.6 g |
| Byk 052 (defoamer) | 0.3 g |
| Bayferrox 130M (iron oxide pigment) | 5.0 g |
| Micro talc AT-1 ($CaCO_3$) | 12.0 g |
| Zinc phosphate | 12.0 g |
| EWO ($BaSO_4$) | 5.6 g |

Solvent Mixture:

| | |
|---|---|
| Methyl isobutyl ketone | 19.2 g |
| Isobutanol | 3.8 g |

Hardener:

Ancamide 700X75

With vigorous stirring (Dispermat, 30 minutes/8500 s$^{-1}$) 1% of the inventive products is stirred into the test formulation. The formulation is then cooled to 20° C. and diluted with the solvent mixture.

Then the gel build-up is evaluated.

After 24 hours the hardener is added with stirring and the formulation is applied with a graduated doctor blade. When curing has taken place, the film thickness achieved is assessed.

| Example | 2 K system | Gel strength | Film thickness |
|---|---|---|---|
| Control | 1 | no gel | 200 μm |
| Byk 410 | 1 | no gel | 450 μm |
| Control | 2 | no gel | 100 μm |
| Byk 410 | 2 | no gel | 300 μm |
| Example I | 1 | strong gel | 800 μm |
| Example II | 1 | strong gel | 850 μm |
| Example III | 2 | strong gel | 750 μm |
| Example IV | 1 | strong gel | 1000 μm |
| Example V | 2 | strong gel | 800 μm |

Key to Trade Names:
Epikote 1001: polyepoxide based on bisphenol A (Shell)
Epikote 834: polyepoxide based on bisphenol A (Shell)
Byk 410: urea urethane, dilution in N-methylpyrrolidone
Jeffamine M 600: alkyl polyether amine, MW 600 (Huntsman)
Jeffamine M 2070: alkyl polyether amine, MW 2000 (Huntsman)
Jeffamine ED 900: alkyl polyether diamine, MW 900 (Huntsman)
Jeffamine ED 2003: alkyl polyether diamine, MW 2000 (Huntsman)
Ancamide 700-X-75: polyamide/epoxide adduct (Air Products)

The invention claimed is:
1. A biuret compound of the general formula

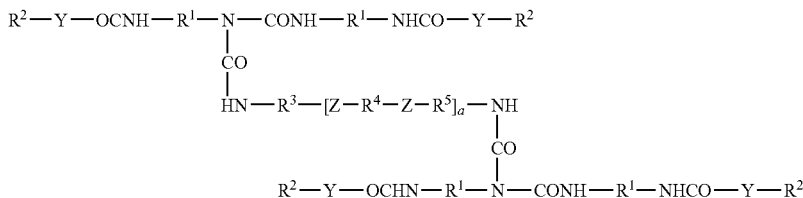

in which $R^1$ is $C_2$-$C_{18}$ alkylene, cycloalkylene, arylene or aralkylene, Y is —O— and/or —NH—, $R^2$ is $C_4$-$C_{22}$ alkyl, $C_3$-$C_{18}$ alkenyl, cycloalkyl, aralkyl, $C_mH_{2m+1}$(O—$C_nH_{2n}$)$_x$—(O—CH($C_6H_5$)—$CH_2$)$_u$—, $C_mH_{2m+1}$(OOC—$C_vH_{2v}$)$_x$—, X—$C_6H_4$—(O—$C_nH_{2n}$)$_x$—(O—CH($C_6H_5$)—$CH_2$)$_u$—, or a polyalkoxy monoalcohol radical, where m=1-22, n=2-4, x=0-15, u=0-15, v=4-5, X is $C_1$-$C_{12}$ alkyl, —($C_6H_5$)$_{1-4}$ and $R^3$, $R^4$ and $R^5$ are independently chosen from $C_2$-$C_{18}$ alkylene, cycloalkylene, arylene or aralkylene, Z is —COO—, NHCO—, NHCOO—, NHCONH— and/or mixtures thereof and a is 1-20.

2. A biuret compound according to claim 1, wherein the radical $R^2$ is a polyalkoxymonoalcohol radical containing ethylene oxide and/or propylene oxide and/or butylene oxide groups.

3. A process for preparing a biuret compound according to claim 1, comprising reacting a uretdione of the general formula (A)

$$R^2-Y-OCNH-R^1-N\underset{\underset{O}{\overset{\overset{O}{\|}}{C}}}{\underset{\underset{\|}{C}}{\phantom{X}}}N-R^1-NHCO-Y-R^2 \quad (A)$$

in which:
 $R^1$ is $C_2$-$C_{18}$ alkylene, cycloalkylene, arylene or aralkylene,
 Y is —O— and/or —NH—,
 $R^2$ is $C_4$-$C_{22}$ alkyl, $C_3$-$C_{18}$ alkenyl, cycloalkyl, aralkyl, $C_mH_{2m+1}(O-C_nH_{2n})_x-(O-CH(C_6H_5)-CH_2)_u-$, $C_mH_{2m+1}(OOC-C_vH_{2v})_x-$, $X-C_6H_4-(O-C_nH_{2n})_x-(O-CH(C_6H_5)-CH_2)_u-$, or a polyalkoxy monoalcohol radical,
 where m=1-22, n=2-4, x=0-15, u=0-15, v=4-5, and
 X is $C_1$-$C_{12}$ alkyl, or —$(C_6H_5)_{1-4}$,
with a diamine of the general formula (B)

$$H_2N-R^3-[Z-R^4-Z-R^5]_a-NH_2 \quad (B)$$

in which:
 $R^3$, $R^4$ and $R^5$ are independently chosen from $C_2$-$C_{18}$ alkylene, cycloalkylene, arylene or aralkylene,
 Z is —COO—, NHCO—, NHCOO—, NHCONH— and/or mixtures thereof
 and a is 1-20.

4. A process for preparing a biuret compound according to claim 2, wherein compounds of the formulae (A) and (B) are reacted at a reaction temperature between 60° C. and 120° C.

5. A process for preparing a biuret compound according to claim 2 wherein the molar ratio of the urethane- and/or urea-containing polymer to polyamine is between 1:0.3 and 1:0.7.

6. A rheology control agent comprising a composition containing a biuret compound of the general formula in which:
 $R^1$ is $C_2$-$C_{18}$ alkylene, cycloalkylene, arylene or aralkylene, Y is —O— and/or —NH—, $R^2$ is $C_4$-$C_{22}$ alkyl, $C_3$-$C_{18}$ alkenyl, cycloalkyl, aralkyl, $C_mH_{2m+1}(O-C_nH_{2n})_x-(O-CH(C_6H_5)-CH_2)_u-$, $C_mH_{2m+1}(OOC-C_vH_{2v})_x-$, $X-C_6H_4-(O-C_nH_{2n})_x-(O-CH(C_6H_5)-CH_2)_u-$, or a polyalkoxy monoalcohol radical, where m=1-22, n=2-4, x=0-15, u=0-15, v=4-5, X is $C_1$-$C_{12}$ alkyl, —$(C_6H_5)_{1-4}$ and $R^3$, $R^4$ and $R^5$ are independently chosen from $C_2$-$C_{18}$ alkylene, cycloalkylene, arylene or aralkylene, Z is —COO—, NHCO—, NHCOO—, NHCONH— and/or mixtures thereof and a is 1-20.

7. A thixotropic coating composition comprising a biuret compound according to claim 6 in combination with a coating system such that the composition displays anti-sag and/or anti-settling properties.

\* \* \* \* \*

$$R^2-Y-OCNH-R^1-\underset{\underset{\underset{\underset{R^2-Y-OCHN-R^1-N-CONH-R^1-NHCO-Y-R^2}{|}}{CO}}{HN-R^3-[Z-R^4-Z-R^5]_a-NH}}{\overset{|}{\underset{|}{N}}}-CONH-R^1-NHCO-Y-R^2$$

UNITED STATES PATENT AND TRADEMARK OFFICE
CERTIFICATE OF CORRECTION

PATENT NO.       : 7,652,166 B2                                        Page 1 of 1
APPLICATION NO.  : 11/400721
DATED            : January 26, 2010
INVENTOR(S)      : Haubennestel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 959 days.

Signed and Sealed this

Twenty-eighth Day of December, 2010

David J. Kappos
*Director of the United States Patent and Trademark Office*